United States Patent [19]

Hori et al.

[11] Patent Number: 4,947,678

[45] Date of Patent: Aug. 14, 1990

[54] METHOD FOR MEASUREMENT OF VISCOSITY CHANGE IN BLOOD OR THE LIKE AND SENSOR THEREOF

[75] Inventors: Tomoshige Hori, Kitamoto; Yasuhiko Shiinoki, Tokyo; Kensuke Itoh, Kodaira, all of Japan

[73] Assignee: Snow Brand Milk Products Co., Ltd., Hokkaido, Japan

[21] Appl. No.: 319,192

[22] Filed: Mar. 6, 1989

[30] Foreign Application Priority Data

Mar. 7, 1988 [JP] Japan .................................. 63-53082
Mar. 18, 1988 [JP] Japan .................................. 63-64776

[51] Int. Cl.$^5$ ............................................. C01N 25/18
[52] U.S. Cl. ......................................... 73/54; 73/64.1; 374/21
[58] Field of Search .................... 338/28, 30; 374/21, 374/43; 73/54, 64.1; 324/65 R

[56] References Cited

U.S. PATENT DOCUMENTS

| | | | |
|---|---|---|---|
| 845,413 | 2/1907 | Haagn .................................. | 338/28 |
| 1,860,541 | 5/1932 | Hebler .................................. | 338/28 |
| 2,685,015 | 7/1954 | Weiller .................................. | 338/28 |
| 3,516,282 | 6/1970 | Leach et al. ........................ | 374/21 |
| 3,678,751 | 7/1972 | Mead et al. .......................... | 338/28 |
| 3,748,624 | 7/1973 | Yazawa et al. ...................... | 338/30 |
| 3,821,643 | 6/1974 | Bostick et al. ...................... | 73/64.1 |
| 4,578,988 | 4/1986 | Hori et al. ............................ | 73/54 |
| 4,611,928 | 9/1986 | Hori et al. ............................ | 73/64.1 |

FOREIGN PATENT DOCUMENTS

| 259252 | 3/1988 | European Pat. Off. ............. | 73/64.1 |
|---|---|---|---|
| 1454816 | 11/1986 | United Kingdom ................. | 338/28 |

*Primary Examiner*—Hezron E. Williams
*Attorney, Agent, or Firm*—Griffin, Branigan & Butler

[57] ABSTRACT

Here is disclosed a method for measurement of viscosity change in blood or the like comprising steps of disposing a sensor including of an endothermic or exothermic element in blood or the like, stimulating blood or the like so as to cause a viscosity change therein and detecting the viscosity change by continuously measuring any one of changes occurring respectively in an average temperature $\theta w$ or a surface temperature $\theta s$ of the sensor containing therein the endothermic or exothermic element, a differential temperature $\theta w - \theta \infty$ or $\theta s - \theta \infty$ between a temperature $\theta \infty$ of blood or the like and $\theta w$ or $\theta s$, a kinematic viscosity $\nu$ of blood or the like and a heat transfer coefficient on the sensor surface. Such measurement may be performed by a sensor comprising an electric insulator through which lead wire extends, metallic wire wound around the electric insulator and connected at opposite ends to the portions of the lead wire exposed on the surface of the electric insulator, and a portion of the electric insulator, around which the metallic wire is wound, being coated with suitable material.

5 Claims, 7 Drawing Sheets

METHOD FOR MEASUREMENT OF VISCOSITY CHANGE IN BLOOD OR THE LIKE AND SENSOR THEREOF

BACKGROUND OF THE INVENTION

The present invention relates to a method for measurement of viscosity change, for example, a blood coagulation process, as well as a sensor used to perform said method.

Generally, determination of a viscosity change occurring in blood or the like is important to know actual conditions of blood or the like and, for example, enables a blood type to be easily identified.

Furthermore, the determination of the viscosity change has been commonly used to diagnose so-called hyperviscosity diseases such as cerebral infarction and myocardinal infarction.

Especially, blood coagulation is particularly important and determination of the coagulation time has been most commonly used for diagnosis of various diseases such as haemophilia, von Willebrand's disease, Christmas disease and hepatic diseases. Pathologically, it has also been put in practice to know a condition of immune reaction by reacting plasma in blood with antigen or antibody.

Typical method for measurement of blood coagulation time which have conventionally employed include those relying on measurement of prothrombin time (PT), measurement of activated partial thromboplastin time (APTT), measurement of thrombin time, fibrinogen test and hepaplastin test.

Typical methods for examination of immune reaction include those relying on examination or measurement of complement supply reaction, fluorescent reaction and enzyme immunity.

With the conventional methods for measurement of viscosity change in blood or the like, determination of coagulation or other phenomena have been macrographically made in most cases, even through these methods have utilized stimulators and test reagents which are commercially available and contain therein predetermined stabilized ingredients. Subjective judgment of the operator has necessarily limited the reliability of measurements and the measuring procedure usually repeated to improve such reliability of measurement has often resulted in unevenness of the measurements.

It is also well known to measure blood coagulation time by use of a mechanical apparatus, for example, through determination of prothrombin time by use of spectrophotometer. However, such method of well known art is disadvantageous in that any disturbance on top of liquid to be tested will cause light scattering which, in turn, will cause a measurement error.

Not only this method utilizing the spectrophotometer but also the other methods of prior art by which the blood coagulation time is measured by use of the mechanical apparatus have inconveniently been complicated also in their mechanisms.

The inventors disclosed a method for measurement of physical property change occurring in liquid or the like in Japanese Disclosure Gazette No. 1985-152943. The disclosed invention proposes, as a part thereof, the method closely related to the present invention, i.e., the method for detection of any thrombus formed on the inner wall of artificial blood vessel through a change of heat transfer coefficient as sensed by a sensor utilizing metallic wire which is fixedly arranged in the inner wall of said artificial blood vessel. However, such method intends only to detect formation of thrombus on the inner wall of the artificial blood vessel but not to detect any abnormal condition occurring in blood or plasma itself.

SUMMARY OF THE INVENTION

A primary object of the present invention is to overcome the above-mentioned disadvantages by providing a method for measurement of a viscosity change occurring in blood or the like and a sensor used to perform the method which can be commonly used for various kinds of measurement concerning the viscosity change in blood or the like, without being prone to erroneous measurement.

According to the present invention, the above-mentioned object is achieved by a method for measurement of viscosity change in blood or the like, said method comprising steps of disposing a sensor comprising an endothermic or exothermic element in blood or the like, stimulating said blood or the like, e.g., to cause clotting so as to cause a viscosity change therein and detecting said viscosity change by continuously measuring the changing values of one or more of an average temperature $\theta w$ of said sensor or a surface temperature $\theta s$ of said sensor, a differential temperature $\theta w - \theta \infty$ or $\theta s - \theta \infty$ between a temperature $\theta \infty$ of blood or the like and $\theta w$ or $\theta s$, a kinematic viscosity $\nu$ of blood or the like and a heat transfer coefficient $\alpha$ on said sensor surface.

Such method for measurement of viscosity change in blood or the like may be effectively performed by using a sensor for measurement of viscosity change on blood or the like comprising an electric insulator through which lead wire extends, metallic wire wound around said electric insulator, said metallic wire being connected at opposite ends to the portions of said lead wire exposed on the surface of said electric insulator, and a portion of said electric insulator around which the metallic wire is wound being coated, or by using the other suitable sensors, for example, the sensor corresponding to the sensor as disclosed in U.S. patent application Ser. No. 224099 but miniaturized to the order of $\phi = 0.6$ mm and $l = 4$ mm.

Generally, a major portion of the time required for blood coagulation is a period elapsing before formation of activated thromboplastin in blood and the reaction slowly goes on. Thereafter, transformation from fibriogen to fibrin rapidly occur. Then, blood loses its fluidity and becomes coagulated.

During such process of blood coagulation, a viscosity change occurs in blood and simultaneously various values related to the sensor comprising the endothermic or exothermic element and disposed in blood also correspondingly change. Specifically, for example the average temperature $\theta w$ of the sensor, the surface temperature $\theta s$ of the sensor, the differential temperature $\theta w - \theta \infty$ or $\theta s - \theta \infty$ between the temperature of fluid such as blood and $\theta w$ or $\theta s$, respectively, and the heat transfer coefficient $\alpha$ on the surface of the sensor change in their respective numerical values.

It is also well known that the changes in these numerical values are in functional relationship with the kinematic viscosity of blood (see Introduction in "Journal of National Food Engineering Society", Jan., 1988).

Thus, these changes may be determined intermittently or continuously to obtain a kinematic viscosity or an index value related to the kinematic viscosity and thereby to detect a viscosity change of blood.

In immunity reaction system, the immunity reaction will be measured as a blood viscosity changes by the sensor in the same manner as has been mentioned above, or the sensor having antibody such as IgG fixed on the surface thereof so as to react with lactopherin contained in plasma, when a plurality of spheric plastic-latex particles are added into blood so that antigen/antibody reaction may occur on surfaces or these spheric particles which are then agglutinated together as a result of this reaction.

BRIEF DESCRIPTION OF THE DRAWING

These and other objects as well as advantages of the present invention will become clear by the following description of preferred embodiments of the present invention with reference to the accompanying drawings, wherein.

and the abscissa indicates elapsing time.

and the abscissa indicates elapsing time.

and the abscissa indicates elapsing time.

DETAILED DESCRIPTION OF THE INVENTION

First, the method according to the present invention will be discussed in reference with FIG. 1 and FIGS. 5 through 10.

It has already been described that the variable values $\theta s$, $\theta w$, $\theta s - \theta\infty$, $\theta w - \theta\infty$, $\alpha$ and $\nu$ change as blood viscosity changes.

Now, a relationship between the differential value $\theta s - \theta\infty$ ($\theta s$: sensor surface temperature; $\theta\infty$: blood temperature) and the kinematic viscosity of blood will be considered by way of example.

Concerning the relationship established between the steady state heat transfer coefficient $\alpha$ and the difference $\theta s - \theta\infty$, the steady state heat transfer coefficient $\alpha$ is given by a following equation:

$$\alpha = \frac{Q}{A(\theta s - \theta\infty)} \quad (1)$$

where Q(W) represents the heat generated in the sensor probe and transferred to the surrounding liquid or heat flux and A(m²) represents the surface area of the sensor.

Accordingly, if both "Q" and "A" in equation (1) are known, the heat transfer coefficient $\alpha$ can be obtained from said differential temperature $\theta s - \theta\infty$.

It should be understood that, when the sensor is cylindrical, the sensor surface area "A" can be calculated so far as the diameter "d" and the length "l" of this cylindrical sensor are known, because $A \approx \pi dl$ in such case.

Then, the relationship between the differential temperature $\theta s - \theta\infty$ and the kinematic viscosity $\nu$ will be considered.

The sensor is disposed, for example, in stationary distilled water of which the physical property values is already known, and then applied with constant current, e.g., DC constant current which may have various values while a differential temperature $\theta s - \theta\infty$ between said distilled water and the (heated) sensor is measured. This procedure allows a relationship to be established among the Nusselt number Nu corresponding to the dimensionless number of the heat transfer coefficient, the Prandtl number Pr corresponding to the dimensionless number of the kinematic viscosity and the Grashof number Gr corresponding to the dimensionless number of the temperature difference, i.e., an equation generally representing free convection heat transfer around said sensor in the form, for example, of $$Nu = Co \, Gr^{C1} \, Pr^{C2} \quad (2)$$

where Co, C1 and C2 represent constants.

Nu, Gr and Pr can be expressed by following equations:

$$Nu = \alpha L/\lambda \quad (3)$$

$$Gr = L^3 g\beta(\theta s - \theta \infty)/\nu^2 \quad (4)$$

$$Pr = \nu/a \quad (5)$$

where "L" represents typical length (m), $\lambda$ represents thermal conductivity (W/mK), "g" represents gravitational acceleration (m/s²), $\beta$ represents coefficient of volumetric expansion (1/K), represents kinematic viscosity (m²/s), and "a" represents thermal diffusivity (m²/s).

Accordingly, from the equations (2) through (5) as set forth above, the kinematic viscosity can be expressed by a following equation:

$$\nu^{2C1-C2} = C_0 g^{C1} A L^{3C1-1} Q^{-1} \lambda \beta^{C1} a^{-C2} (\theta s - \theta \infty)^{C1+1} \quad (6)$$

When platinum wire adapted to be applied with current "i" and thereby to be heated is employed as the sensor, $$Q = Ri^2 \quad (7)$$

where "R" represents the electric resistance ($\Omega$) of the platinum wire used as the sensor and "i" represents the value "A" of direct electric current applied to the sensor.

In the above-mentioned equation (6), g, "A" and "L" represent constants.

Further when the fluid include a large quantity of water or the composition of the fluid remain relatively unchanged, it can be assumed that $\lambda$, $\beta$ and $a$ respectively change in ranges sufficiently smaller that the range in which changes, so that the kinematic viscosity $\nu$ can be ultimately expressed by a following equation as a function exclusively of the differential temprature $\theta s - \theta \infty$ and the heat flux "Q":

$$\nu^{2C1-C2} = C_3 Q^{-1}(\theta s - \theta \infty)^{C1+1} \quad (8)$$

where $C_3$ represents a constant.

Using blood as the fluid (F) and applying the sensor (S) with current so as to maintain the heat flux "Q" constant, the differential temperature $\theta s - \theta \infty$ between blood and the surface of the sensor may be measured to obtain a kinematic viscosity $\nu$ and thereby to detect a change in blood viscosity.

The above-mentioned blood temperature $\theta \infty$ may be measured by use of the resistance thermometer comprising platinum and said $\theta s$ may be measured by employing the invention disclosed in the prior Japanese Disclosure Gazette No. 1988-217261 (corresponding to U.S. patent application Ser. No. 157261) of the inventors. Accordingly from Japanese Disclosure Gazette No. 1988-217261 the relationship between the sensor surface temperature $\theta s$ and the sensor average temperature $\theta w$ is expressed by;

$$\theta s = \theta w - Ao \cdot i^2 (1 + \alpha w \theta w) \quad (9)$$

where
$\alpha w$: temperature coefficient of electric resistance
i: value of current applied to the sensor
Ao: constant.
And $\theta w$ is expressed by $$\theta w = (V/i \cdot Ro - 1)/\alpha w \quad (10)$$

where
Ro: electric resistance developed in the sensor metallic wire at 0° C.
V: value of voltage across the sensor.

Therefore, $\theta w$ can be calculated from the voltage value "V" and the current value "i" of the sensor, and $\theta s$ can be calculated from $\theta w$. Furthermore, from equation (9) and (10) as set forth above, $\theta s$ can be expressed by a function of both the voltage value and the current value, $$\theta s = f(V, i) \quad (11)$$

Accordingly, $\theta s$ can be calculated also from the voltage value and the current value.

When the blood temperature $\theta \infty$ and the sensor average temperature $\theta w$ is measured by use of the resistance thermometer, $\theta s$ can be calculated also by using a following equation:

$$\theta s = \theta \infty + Co'(\theta w - \theta \infty)^{C1'} \quad (12)$$

or $$\theta s = \theta \infty + Co''(\theta w - \theta \infty) \quad (13)$$

Co', Co'', C1': specific constants of the sensor.

In this way, the viscosity change occurring in blood or the like can be determined by measuring the variable values of $\theta s$, $\theta w$, $\theta s - \theta \infty$, $\theta w - \theta \infty$, $a$ and $\nu$. Now a method for determination of a viscosity change and, therefore, a specific coagulation time of blood from a change of $\theta s - \theta \infty$, based on a result of the experiment conducted in connection with $\theta s - \theta \infty$, will be explained.

Figure 1:
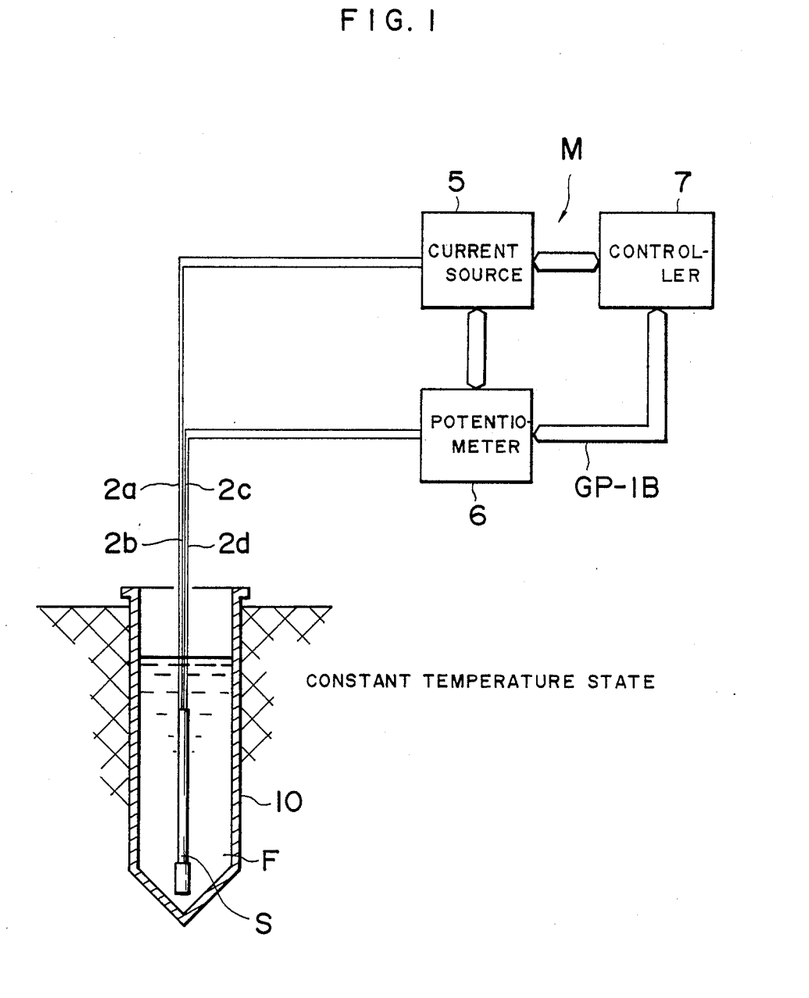
FIG. 1 is a schematic diagram illustrating, partially in section, how the sensor constructed in accordance with the present invention is used.

For the experiment, an apparatus as shown by FIG. 1 was used.

Referring to FIG. 1, a sensor "S" is placed in a quantity of fluid "F" such as blood contained in a vessel 10 and, in a measuring system "M", a pair of current lead wire 2a, 2b connected to platinum wire are connected to a current source 5 for energization while another pair of voltage lead wires 2c, 2d are connected to a potentiometer 6 for voltage measurement so that electrical resistance of the sensor can be measured on the basis of four wire method.

In the measuring system "M", the DC power source 5, the digitalvoltmeter 6 and a controller 7 are connected one to another by GP-IB (general purpose interface bus).

With the platinum wire 3 being applied with current so as to maintain the heat flux thereof constant, by continuously measuring values of voltage impressed to the platinum wire 3, the sensor average temperature $\theta w$, the surface temperature of the sensor $\theta s$, the differential temperature $\theta s - \theta \infty$ between blood and the surface of the sensor, and the differential temperature $\theta w - \theta \infty$ between blood and the sensor is determined from the equations (9) through (13).

Additionally there is the difference between the method of measuring the blood temperature $\theta \infty$ by one sensor and that by two sensor, which is described as follows;

In case of one sensor,

Step 1; the sensor is applied with direct current of about 100 $\mu$A or 1 mA.

Step 2; the measurement of voltage values V impressed to the platinum wire of the sensor.

Step 3; the blood temperature $\theta\infty$ can be calculated from the equation (10) and the voltage value V.

Step 4; further the sensor is applied with direct current of more than 1 mA i.e., 20 mA or 60 mA.

Step 5; the same as Step 2.

Step 6; the sensor average temperature $\theta w$ can be calculated by the same method of Step 3.

Step 7; the differential temperature $\theta s - \theta \infty$ can be calculated from the equation (12).

Repeating the measurement and the calculation of Step 5 through 7, the changing value of $\theta s - \theta \infty$ with respect to the elapsing time can be obtained.

In case of two sensor $S_1$, $S_2$,

Step 1: the sensor $S_1$ is applied with direct current of about 100 μA or 1 mA

Step 2: the measurement of voltage values $V_1$ impressed to the platinum wire of the sensor $S_1$.

Step 3: the blood temperature $\theta\infty$ can be calculated from the equation (10) and the voltage value $V_1$.

Step 4: the sensor $S_2$ is applied with direct current of more than 1 mA, i.e., 20 mA or 60 mA.

Step 5: the measurement of voltage value $V_2$ impressed to the platinum wire of the sensor $S_2$.

Step 6: the sensor average temperature $\theta w$ can be calculated from the equation (10) and the voltage value $V_2$.

Step 7: the differential temperature $\theta s - \theta \infty$ can be calculated from the equation (12).

Repeating the measurement and the calculation of Step 2 through 3 and Step 5 through 7, the changing value of $\theta s - \theta \infty$ with respect to the elapsing time can be obtained.

Figure 2:
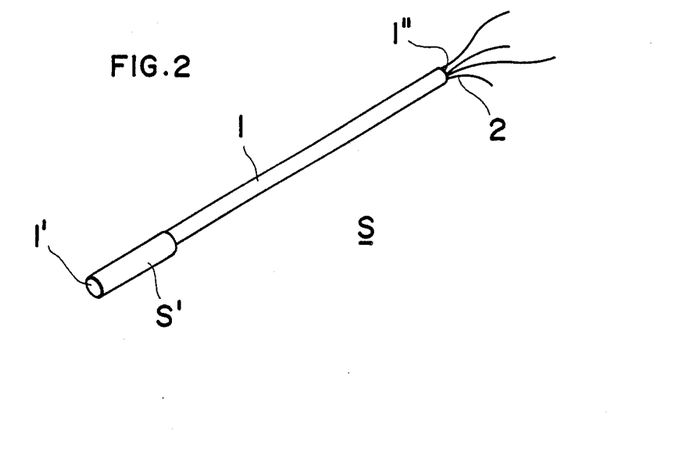
FIG. 2 is a perspective view of the sensor constructed as one embodiment of the present invention.
Figure 3:
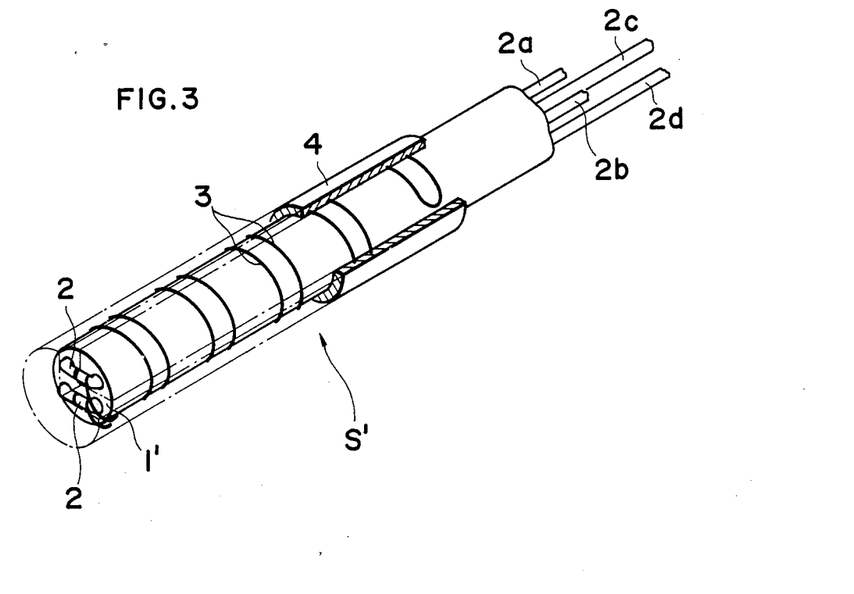
FIG. 3 is a detailed view corresponding to FIG. 2 being partially broken away.
Figure 4:
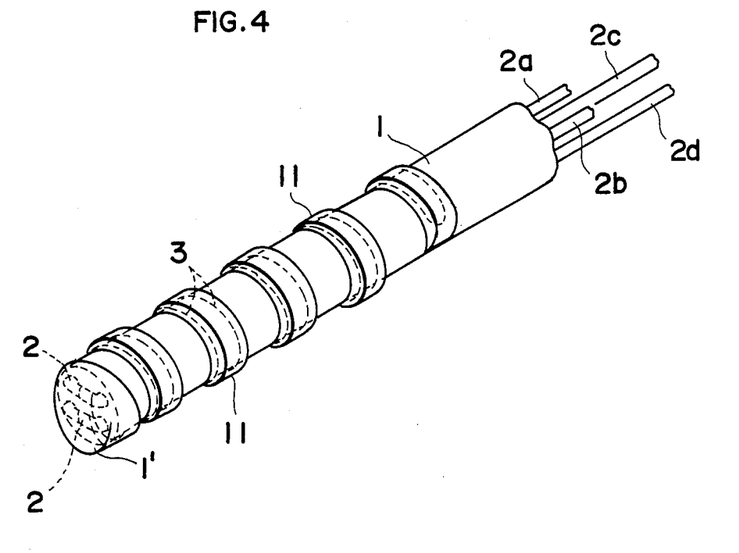
FIG. 4 is a perspective view of the sensor constructed as another embodiment of the present invention.

While the sensor as has been described in reference with FIGS. 2 through 4 was used in this embodiment, any other types of sensor may be used so far as the sensor comprises an endothermic element or an exothermic element.

The result of the experiments conducted by the inventors will be set forth below.

In the experiments of the inventors, samples of human normal plasma (VNC) were injection-added with various reagents and coagulation processes occurring thereafter were continuously measured by use of the sensor.

EXAMPLE 1

Each 0.1 ml of normal whole blood, normal plasma, abnormal whole blood and abnormal plasma was mixed-injection-added with 0.2 ml of clotting factor stimulator such as tissue thromboplastin and calcium chloride, and then the prothrombin time (PT) was measured.

Each quantity of liquid to be tested was prepared in a tube (diameter 8 mm) provided with the sensor comprising platinum wire which presents electric resistance of 50Ω at a temperature of 0° C., and the sensor was heated by applying thereto direct electric current of about 40 mA or about 60 mA.

Figure 5A:
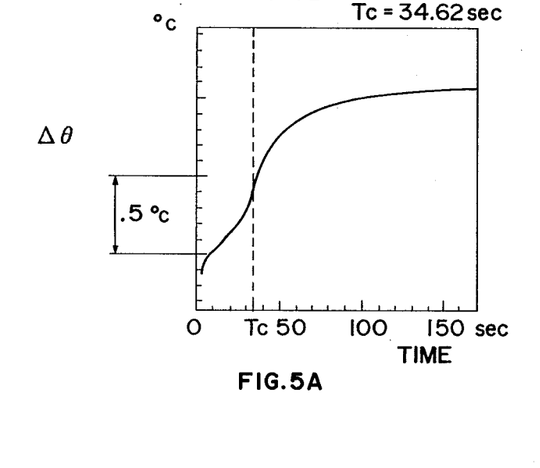
FIGS. 5A and 6A are graphic diagrams respectively plotting the prothrombin time using abnormal plasma and normal plasma, in which the ordinate indicates a difference $\Delta\theta = \theta s - \theta\infty$ and the abscissa indicated elapsing time.
Figure 5B:
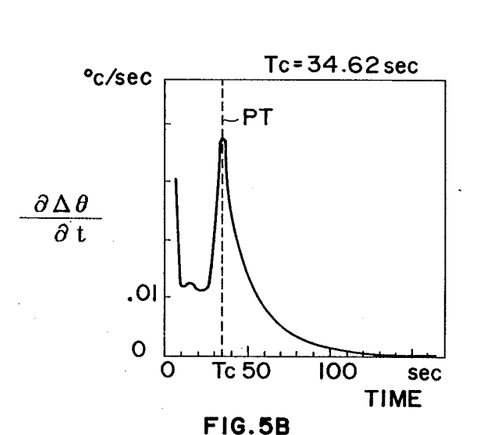
FIGS. 5B and 6B are graphic diagrams respectively plotting the changing rates of $\Delta\theta$ with respect to the elapsing time given in FIGS. 5A and 6A, in which the ordinate indicates $$\frac{\partial \Delta\theta}{\partial t}$$
Figure 6A:
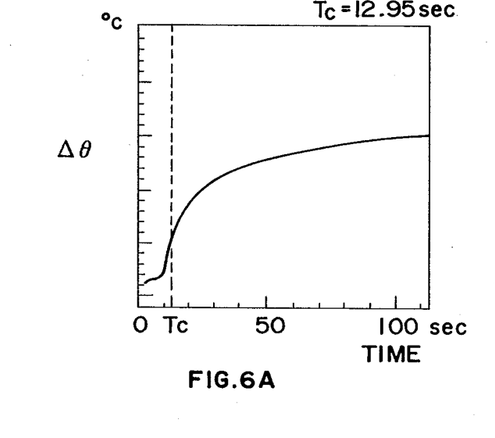
Figure 6B:
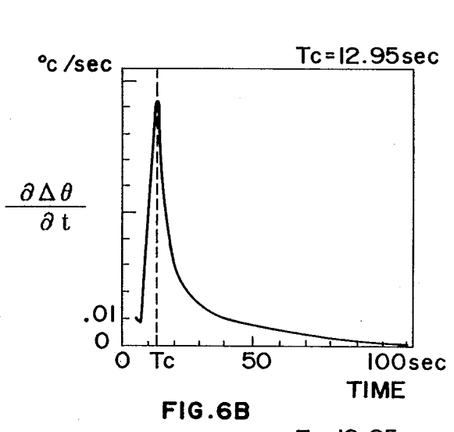

FIGS. 5A and 5B show the differential temperature $\theta s - \theta \infty$ measured as a function of the elapsing time using abnormal plasma as liquid to be tested, with the sensor heating current of about 40 mA, and FIGS. 6A and 6B are similar to FIGS. 5A and 5B except that normal plasma was used as liquid to be tested with the sensor heating current of about 40 mA.

In the experiment corresponding to FIGS. 5A, 5B and FIGS. 6A, 6B, a point of inflection at which the changing rate of the differential temperature $\theta s - \theta \infty$ sharply decreases as the time elapses was determined as a fixed point and thereby the prothrombin time (PT) was measured to be 34.6 sec and 13.0 sec, respectively.

TABLE 1

| Pt, VNC<br>i = 40mA | 10%<br>34.6 sec<br>(FIG. 5) | 100%<br>13.0 sec<br>(FIG. 6) |
|---|---|---|

In the Table 1, 10% means that a quantity of normal plasma was diluted 10 times by physiological saline so as to prepare a sample of plasma just as collected from a patient at extreme morbidity (e.g., almost at dead condition) and 100% means that the sample comprises only normal plasma.

EXAMPLE 2

Each 0.2 ml of normal whole blood, normal plasma, abnormal whole blood and abnormal plasma was mixed-injection-added with 0.1 ml of clotting factor stimulator comprising kaolin, phospholipid, cerite, silicic acid, elaidic acid or the like, and then the activated partial thromboplastin time (APTT) was measured.

Each quantity of liquid to be tested was prepared in a tube (diameter 8 mm) provided with metallic wire serving as the sensor and the sensor was heated by applying thereto current of about 40 mA.

Figure 7A:
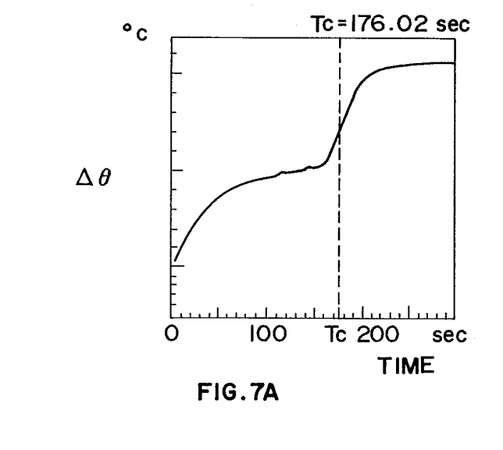
FIGS. 7A and 8A are graphic diagrams respectively plotting the activated partial thromboplastin time using abnormal plasma which is made from normal plasma through dilution by physiological saline and normal plasma, in which the ordinate indicates a difference $\Delta\theta = \theta s - \theta\infty$ and the abscissa indicated elapsing time.
Figure 7B:
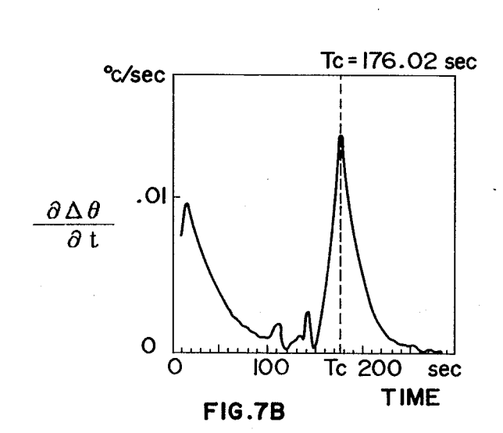
FIGS. 7B and 8B are graphic diagrams respectively plotting the changing rate of said $\Delta\theta$ with respect to the elapsing time given in FIGS. 7A and 8A, in which the ordinate indicates $$\frac{\partial \Delta\theta}{\partial t}$$
Figure 8A:
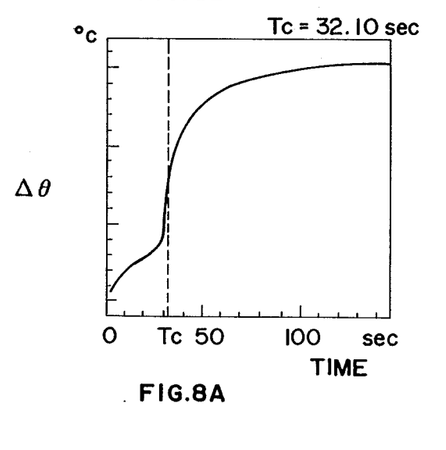
Figure 8B:
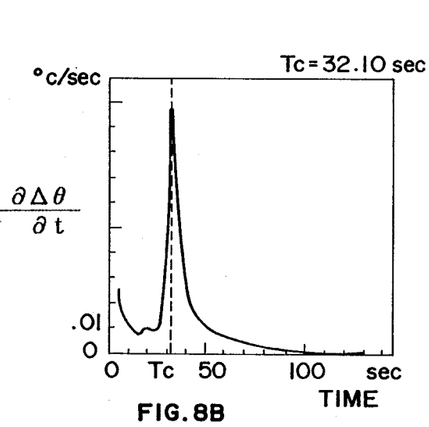

FIGS. 7A and 7B show the differential temperature $\theta s - \theta \infty$ measured as a function of the elapsing time using abnormal plasma as liquid to be tested, with the sensor heating current of about 40 mA, and FIGS. 8A and 8B are similar to FIGS. 7A and 7B except that normal plasma was used as liquid to be tested with the sensor heating current of about 40 mA.

In the experiments respectively corresponding to FIGS. 7A, 7B and FIGS. 8A, 8B, the activated partial thromboplastin times (APTT) were determined to be 176.0 sec and 32.1 sec, respectively, in the same manner as in EXAMPLE 1.

TABLE 2

| APTT, VNC<br>i = 40mA | 10%<br>176.0 sec<br>(FIG. 7) | 100%<br>32.1 sec<br>(FIG. 8) |
|---|---|---|

Meaning of 10% and 100% are same as in Table 1.

EXAMPLE 3

A series of plasma samples was prepared by adjusting their fibrin contents stepwise from 1% to 20% of that normally found in healthy human plasma through dilution thereof by physiological saline, and the thrombin time was determined on these sample by injection-adding 0.2 ml of clotting factor stimulator to 0.1 ml of the respective samples and applying the sensor with current of about 60 mA.

Figure 9A:
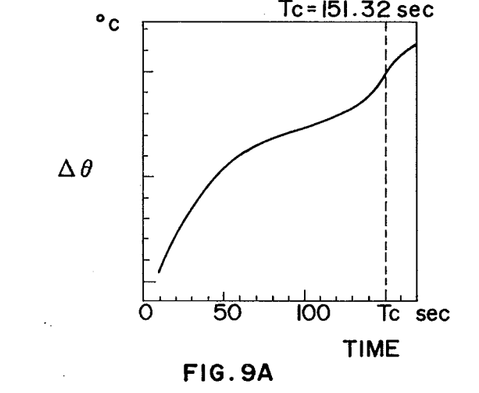
FIGS. 9A and 10A are graphic diagrams respectively plotting the thrombin time using human normal plasma samples having fibrin content of 1% and 20%, in which the ordinate indicates a difference $\Delta\theta = \theta s - \theta\infty$ and the abscissa indicates elapsing time.
Figure 9B:
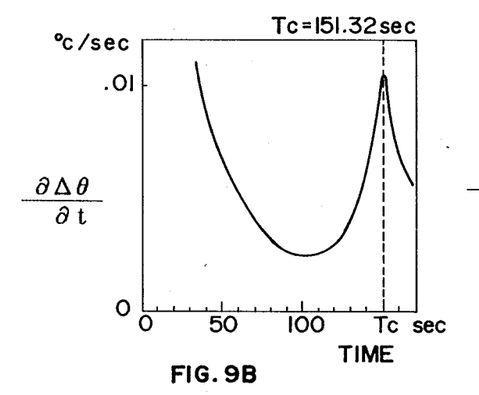
FIGS. 9B and 10B are graphic diagrams respectively plotting the changing rate of said $\Delta\theta$ with respect to the elapsing time given in FIGS. 9A and 10A, in which the ordinate indicates $$\frac{\partial \Delta\theta}{\partial t}$$
Figure 10A:
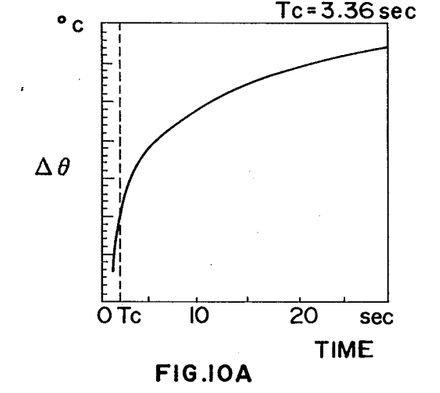
Figure 10B:
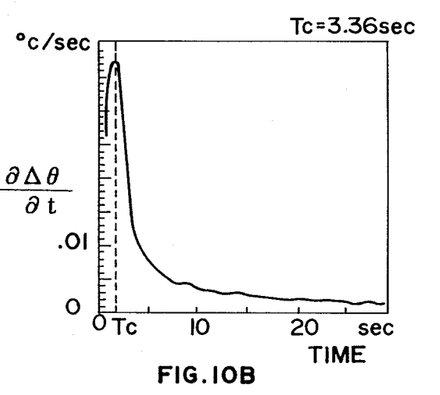

FIGS. 9A and 9B show the differential temperature $\theta s - \theta \infty$ as a function of the elapsing time in the sample of which the fibrin content is 1% of that normally found in healthy human plasma, and FIGS. 10A and 10B show the result obtained on the sample of which the fibrin content is 20% of that normally found in healthy human plasma.

In these experiments of which the results are shown by FIGS. 9A, 9B and FIGS. 10A, 10B, the thrombin times were also determined in the same manner as in Example 1 to be 151.3 sec and 3.4 sec, respectively.

Similarly, the thrombin times were determined, on the samples of which the respective fibrin contents are 2% and 10% of that normally found in healthy human plasma, to be 54.3 sec and 7.7 sec, respectively.

As apparent from three Examples as have been described above, a viscosity change occurring in blood or the like can be detected by determining a change in the value $\theta s - \theta \infty$.

Determination of a change in the kinematic viscosity $\nu$ permits a change in the viscosity of blood or the like to be detected, by finding a point of inflection in the same manner as in the case of $\theta s - \theta \infty$, since the kinematic viscosity $\nu$ can be expressed as a function only of the heat flux "Q" and $\theta s - \theta \infty$ by the equation (8).

Figure 12:
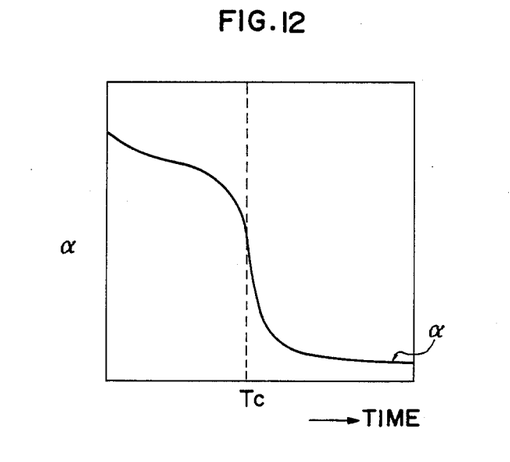
FIG. 12 is a graphic diagram roughly plotting the change in the heat transfer coefficient with respect to the changes of $\theta s$ and $\theta w$ as illustrated in FIG. 11.

The heat transfer coefficient $\alpha$ and $\theta s - \theta \infty$ are reciprocal to each other, since these are in the mutual relationship as expressed by the equation (1). Accordingly, a relationship between a variation of the heat transfer coefficient $\alpha$ and the time "t" can be plotted as a graphic diagram which is reciprocal to the above-mentioned FIGS. 5A, 6A, 7A, 8A, 9A and 10A, and a point of inflection may be determined in the same manner as in the case of $\theta s - \theta \infty$ to detect the viscosity change occurring in blood or the like, as seen in FIG. 12. For example, concerning $\theta w - \theta \infty$, transferring $\theta \infty$ from the right side to the left side in the equation (12) results in a following equation:

$$\theta s - \theta \infty = Co'(\theta w - \theta \infty)^{C1'} \qquad (14)$$

It will be appreciated from this equation (14) that $\theta w - \theta \infty$ is a function of $\theta s - \theta \infty$ and, just as in the case of $\theta s - \theta \infty$, a point of inflection may be determined along the curve of $\theta w - \theta \infty$ to detect a viscosity change occurring in blood or the like.

Figure 11:
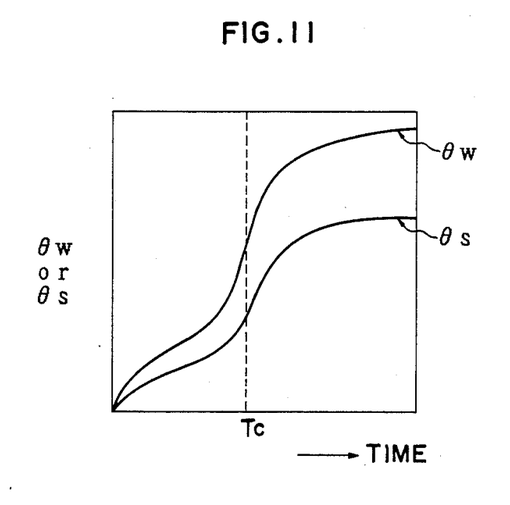
FIG. 11 is a graphic diagram roughly plotting the changes of $\theta s$ and $\theta w$ with respect to the prothrombin time (PT) of normal blood.

$\theta s$ or $\theta \infty$ changes generally as shown by FIG. 11 as the viscosity of blood or the like changes, when the clotting factor stimulator is injection-added to the sample of healthy human blood and then the prothrombin time (PT) is determined. Thus, it is also possible to detect the viscosity change of blood or the like by finding a point of inflection along a curve plotted by the value of $\theta s$ or $\theta \infty$ varying as the viscosity of blood or the like changes. It should be understood that FIG. 12 shows how the heat transfer coefficient $\alpha$ changes with respect to variation of $\theta s$ and $\theta w$ shown in FIG. 11 and the coagulation time (Tc) can be determined by finding a point of inflection along a curve plotted by the heat transfer coefficient $\alpha$.

In this manner, the viscosity change of blood or the like can be easily determined also from respective variations of $\theta s$, $\theta w$, $\theta w - \theta \infty$, $\alpha$ and $\nu$.

As will be apparent from the foregoing description, the method of the present invention enables the viscosity change being important to know actual condition of blood or the like to be easily and exactly detected without interposition of any human subjective judgment.

With a consequence, the other conditions of blood such as the blood type can be also easily identified by the method of the invention, because the manner of coagulation depends on a particular blood type.

Additionally, as has been described in reference with FIG. 7 and 9, even a patient being in such serious condition that the blood coagulation time tends to be prolonged can be diagnosed almost independently of any influence by the inevitable low viscosity. The method of the invention further enables even a small variation occurring in blood to be easily detected, thus minimizing an error possibly occurring in diagnostic measurement and allowing the blood diagnosis to be performed over a wide range.

The method of the invention effectively simplifies the procedure of measurement and, therefore, measurement may be repeated to improve the accuracy.

Moreover, the method of the invention simplifies the construction of the equipment, particularly, the detection sensor used for measurement and correspondingly reduces the cost with respect to the prior art.

While the viscosity change of blood or the like was caused by stimulating blood or the like with addition of clotting factor stimulator in the previously mentioned Examples 1 through 3 of the method according to the present invention, the method of the invention is not limited to such manner of stimulation and antigen or antibody may be brought into contact with or added into blood or the like to stimulate the latter. For example, IgG may be used as the antibody and fixed onto the sensor surface, so as to react with lactopherin so that quantity of lactopherin can be measured.

Stimulation of blood or the like may be also achieved by suitable physical means, for example, by use of high frequency vibration acting on blood or the like or by heating blood or the like itself.

Now the sensor of the present invention will be described in reference with FIGS. 2 through 4 which illustrate one embodiment of the sensor constructed according to the present invention. Referring to FIGS. 2 and 3, 1 designates a cylindrical electric insulator, 2a and 2b or 2c and 2d designates a pair of lead wire extending through said electric insulator 1, and 3 designates platinum wire noninductively wound around the electric insulator 1 so as to form a measuring section "S'".

The pair of lead wire 2a and 2b or 2c and 2d extend from a rear end 1" through the electric insulator 1 slightly beyond a front end 1' of said electric insulator 1 and then U-turn again to extend through said electric insulator 1 beyond said rear end 1". Opposite ends of the platinum wire 3 are electrically connected to two pair of lead wire at their respective U-turn sections by means of spot welding or the like.

The measuring section "S'" around which the platinum wire 3 is wound is coated with glass layer 4.

FIG. 4 illustrates a variant of the sensor constructed in accordance with the present invention. In this embodiment, the platinum wire 3 is noninductively wound around the electric insulator 1 which is, in turn, coated with synthetic resin layer 11.

The sensor of the present invention is made in a manner as will be described below.

A ceramic hollow rod having a length of 50 mm and a diameter of 1.4 mm is used as the electric insulator 1 and the platinum wire having a diameter of 13 $\mu$m is noninductively wound around said ceramic hollow rod so as to define at its front end the measuring section "S'" extending axially along the ceramic hollow rod over a length of 3 mm. Glass pipe is fit around this assembly and heated to be deposited thereon or said assembly is immersed in liquid glass. Alternatively, said assembly may be immersed in resinous monomer dispersed system, then the platinum wire may be heated by energization to promote thermal polymerization around the outer surface of the platinum wire and thereby to form resinous polymer layer around the platinum wire. Here is provided thereby the sensor being capable of analyzing even a small quantity of sample with a high sensibility.

The sensor of this invention may be used in accordance with the procedure as has been described in reference with FIG. 1 to detect the viscosity change in blood or the like.

Specifically, blood is used as the fluid "F", the sensor "S" is applied with current so as to maintain the heat flux "Q" constant and thereby a variation of the differential temperature $\theta s - \theta \infty$ between blood and the surface of sensor can be determined. Moreover, on the grounds that the sensor average temperature $\theta w$ is unchangeable, it can be assumed that the heat flux "Q" is constant so as to keep the direct electric current "i" constant. Based on this variation of $\theta s - \theta \infty$, it is possible to determine the viscosity change occurring in blood or the like.

Furthermore, the variable values such as $\theta w$, $\theta s$, $\theta w - \theta \infty$, $\alpha$ and $\nu$ can be calculated from the previously mentioned equations and these numerical values also enable the viscosity change in blood or the like to be determined.

Experimental use for detection of the viscosity change in blood or the like indicated that the sensor of this invention actually provides the effect just as has previously been described in connection with the method of the invention for detection of the blood viscosity change.

Finally, the sensor of this invention is advantageous in that even a small quantity of sample can be analyzed with a high sensibility and that adhesion of blood ingredients onto the sensor can be sufficiently reduced to facilitate cleaning thereof because the sensor surface is coated with glass or synthetic resin.

While there has been described what is at present considered to be preferred embodiment of the invention, it will be understood that various modifications may be made therein, and it is intended to cover in the appended claims all such modifications as fall within the true spirit and scope of the invention.

What is claimed is:

1. A method of measurement of viscosity changes in blood or the like, comprising:
   (1) providing an electrically conductive sensor which is electrically heatable by passing an electric current therethrough and having means for determining the voltage impressed on said sensor by said electric current;
   (2) immersing said sensor in said blood;
   (3) applying an electric current to said sensor;
   (4) measuring the current applied to the sensor and the voltage impressed on said sensor by said electric current, and calculating therefrom a sensor temperature of at least one of the average sensor temperature and the surface temperature of the sensor;
   (5) measuring the temperature of said blood;
   (6) calculating the difference between the sensor temperature and said blood temperature; and
   (7) detecting changes in the said difference, whereby the changes in the viscosity of the said blood are correspondingly detected.

2. A method as claimed in claim 1, wherein said change in viscosity is caused by adding a coagulation activating material to the blood.

3. A method as claimed in claim 1, wherein said change in viscosity is caused by bringing an antigen or an antibody in contact with the blood or by adding an antigen or an antibody to the blood.

4. A method as claimed in claim 1, wherein said change in viscosity is caused by heating, cooling or agitating the blood.

5. A method as claimed in claim 1 wherein in step (6) the first derivative of the difference between the sensor temperature and the blood temperature is calculated and in step (7) the detected changes in the first derivative correspondingly detect changes in the blood viscosity.

* * * * *